US005724992A

United States Patent [19]
Ip

[11] Patent Number: 5,724,992
[45] Date of Patent: Mar. 10, 1998

[54] INTRA-OPERATIVE BODY IMMOBILIZER

[76] Inventor: Kai Ip, 5 Sandra Rd., Hillsborough, Calif. 94010

[21] Appl. No.: 583,595

[22] Filed: Jan. 5, 1996

[51] Int. Cl.$^6$ .................................................. A61G 15/00
[52] U.S. Cl. ........................... 128/845; 128/846; 128/870; 5/634
[58] Field of Search ................................. 128/845, 846, 128/869, 870; 5/630, 632, 634

[56] References Cited

U.S. PATENT DOCUMENTS

| | | | |
|---|---|---|---|
| 2,133,223 | 10/1938 | Brightman | 5/634 |
| 2,777,138 | 1/1957 | Gallagher | 5/634 |
| 4,579,111 | 4/1986 | Ledesma | 128/870 |
| 4,594,999 | 6/1986 | Nesbit | 128/870 |
| 4,750,478 | 6/1988 | Bergeron | 128/870 |
| 4,949,713 | 8/1990 | Mykietiuch | 128/845 |
| 5,048,136 | 9/1991 | Popitz | 128/870 |
| 5,140,995 | 8/1992 | Uhl | 128/846 |
| 5,337,427 | 8/1994 | Pagano | 128/845 |
| 5,467,782 | 11/1995 | Wiseman | 128/845 |

*Primary Examiner*—Michael A. Brown
*Attorney, Agent, or Firm*—Patent & Trademark Services, Inc.; Joseph H. McGlynn

[57] ABSTRACT

A body immobilization and support device including a generally rigid shell having a back portion which is generally contoured to the back of a patient, and having side engaging portions and shoulder engaging portions to immobilize and support the patient during surgery. The device further includes fasteners to fasten the shell to an operating table and prevent sliding when used in an extreme head down position. The device may include a cushioning pad along the inside of the shell in order to increase patient comfort.

5 Claims, 1 Drawing Sheet

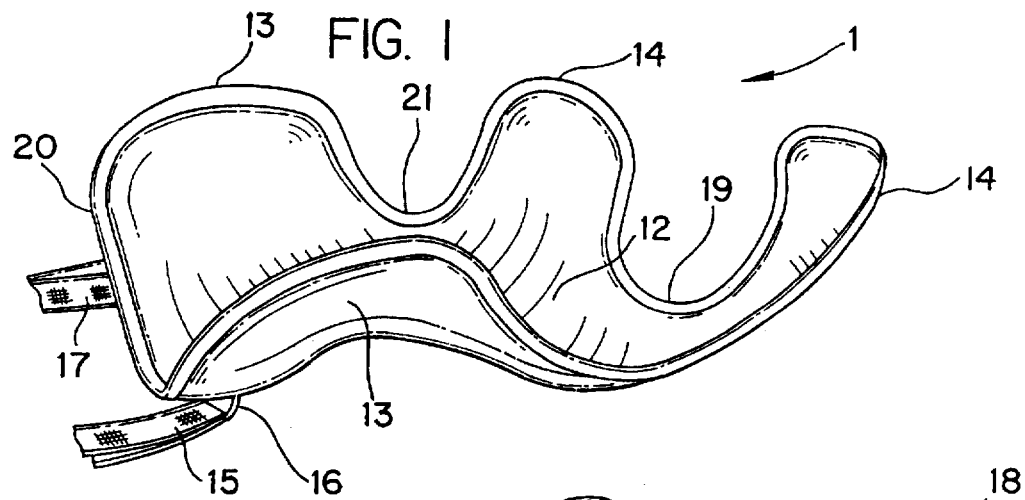
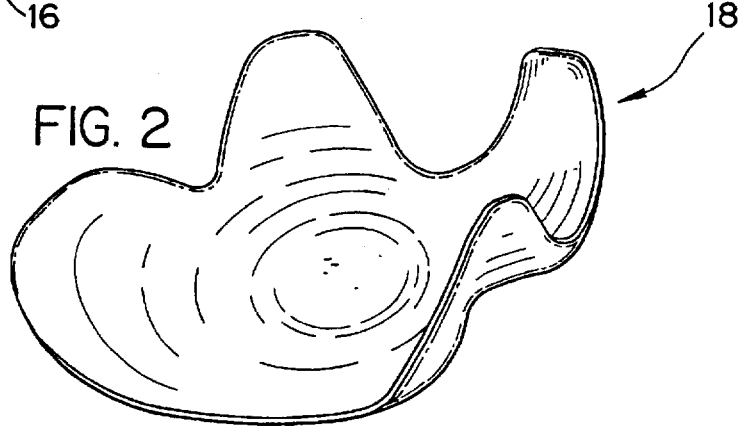
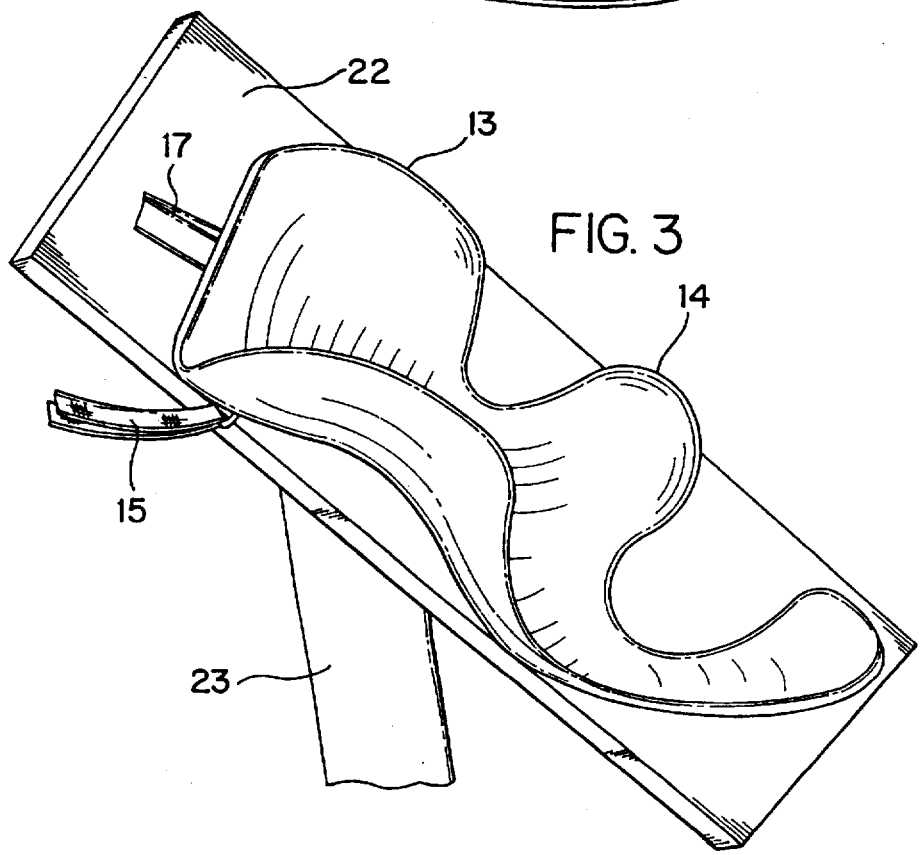

INTRA-OPERATIVE BODY IMMOBILIZER

BACKGROUND OF THE INVENTION

This invention relates, in general, to devices for immobilizing the human body, and, in particular, to such devices for use in holding the patient in deep Trendelendberg (head down) position during surgery. With the advance of laparoscopic surgery, the patient has to be put in extreme head down position in order to move the intestines away from the pelvic organs during surgery.

DESCRIPTION OF THE PRIOR ART

In the prior art various types of body immobilization devices are known. For example, U.S. Pat. No. 4,594,999 discloses a disposable cervical spine board for securing a patients head and body. U.S. Pat. No. 4,750,478 discloses a seat support and restraint system for the handicapped. U.S. Pat. No. 4,579,111 discloses a support pad to support the head and to restrain the arms of a patient. U.S. Pat. No. 5,048,136 discloses a full body support for an infant.

It is well known in the art to use metal bars which are installed at the head of the operating table when a patient has to be placed in extreme head down position in order to prevent the patient from sliding off the operating table. However, the use of metal bars usually causes brachial plexus nerve damage. The present invention is designed to place the patient in a proper position in which the surgeon can operate, and at the same time it is designed to support the patient so there is no pressure on the patient's shoulders. In the past, using metal bar supports, has sometimes caused nerve injury to the patient's shoulders as a result of the weight of the patient's body being directly applied to his/her shoulders for prolonged periods of time.

SUMMARY OF THE INVENTION

The present invention is directed to a body immobilization device for use on an operating table. It consists of a body immobilization and support device including a generally rigid shell having a back portion which is generally contoured to the back of a patient and having side engaging portions and shoulder engaging portions to immobilize and support the patient during surgery. The device further includes fasteners attached to the shell to fasten the shell to an operating table and prevent sliding of the patient when the patient is in an extreme head down position. The device may include a cushioning pad along the entire inside of the shell in order to increase patient comfort.

It is an object of the present invention to provide stable support for a patient placed in an extreme head down position during surgery.

It is an object of the present invention to provide support for a patient during surgery while eliminating brachial plexus nerve injury.

It is an object of the present invention to provide support for a patient during surgery which is comfortable to the patient.

These and other objects and advantages of the present invention will be fully apparent from the following description, when taken in connection with the annexed drawings.

BRIEF DESCRIPTION OF THE DRAWINGS

FIG. 1 is a side view of the present invention.

FIG. 2 is a front view of the pad used with the present invention.

FIG. 3 is a view of the present invention on an operating table in the extreme heads down position.

DESCRIPTION OF THE PREFERRED EMBODIMENT

Referring now to the drawings in greater detail, FIG. 1 shows the body immobilization and support device 1. The device includes a generally rigid shell 11 having a back portion 12 which is generally contoured to the back of a patient and having side engaging portions 13 and shoulder engaging portions 14 to immobilize and support the patient during surgery. The device includes fastening means 15, 17 such as ropes, webbing, straps, or the like to fasten the shell to the operating table. The straps 15, 17 can be attached to the shell by means of rings 16 which are permanently attached to the shell. It should be noted that how the straps are attached to the shell is not critical, and they can be attached by any conventional fastener, or they could be molded into the rigid shell as it is being formed.

Also, even though there are only two straps 15, 17 shown in the drawings, it should be understood that these are merely for illustration purposes. Additional straps can be attached to the shell 11 if needed. In addition the straps can be provided with any conventional securing fasteners such as, but not limited to, buckles or Velcro fasteners to secure the shell to the operating table.

The shell 11 can be molded as a one piece unit, or it can be made in sections which are secured together at a later time such as by, but not limited to, gluing. In addition, the shell can be made in different sizes to fit patients such as small children, adolescents, or adults.

The interior portion of the shell 11 (the part the patient will lie on) can be provided with a pad or cushioning means 18, shown in FIG. 2. The pad 18 can be a separate piece, as shown in FIG. 2, or it can be made unitary with the shell 1. In any event the pad 18 will be formed to fit within the shell 1 and conform to the inside of the shell in order to increase patient comfort. Obviously the pad 18 should be made of a soft, comfortable material such as, but not limited to, foam rubber.

In use, the shell will be secured to the operating table 22, having, for example a movable support 23, before the table is raised into position. The straps 15, 17 will be attached to the table so the shell 1 will be firmly secured. The patient will then be placed within the shell 1 with the patient's neck protruding through slot 19 and their arms protruding slots 21. Additional straps, not shown but similar to straps 15, 17, could be used to secure the patient into the shell if necessary. The table 22 will then be tilted into position such that when in use the patient will be placed in the extreme head down position. The shoulder portions 14, along with the additional straps, not shown, will maintain the patient supported within the shell 1 in such a way that he/she is prevented from sliding down the operating table. The side pieces 13 will also support the patient so they can not roll off the side of the table.

Although the body support device and the method of using the same according to the present invention has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What I claim as my invention is:

1. A body immobilization and support device for use with an operating table which will be tilted during an operation so that the patient is placed in a head down position, comprising:

a generally rigid shell, said shell having a back portion which is generally contoured to the back of a patient, and having side engaging means for preventing said patient from rolling off a side of said operating table, said shell also having a pair of shoulder engaging means for engaging said patient's shoulders for preventing said patient from sliding off an end of said operating table, aperture means extending between said shoulder engaging means for allowing a patient's head to protrude therethrough, and a slot extending between said side engaging means and said shoulder engaging means for allowing a patient's arms to protrude therethrough, whereby said patient's body, when placed in a head down position, will be supported solely by said shoulder engaging means and no weight will be placed on a patient's neck, said shell further including fastening means for securing said shell to said operating table and preventing movement of said shell with respect to said operating table when used in an extreme head down position.

2. The body immobilization and support device as claimed in claim 1, wherein said fastening means are straps permanently attached to said shell and detachably attached to said operating table.

3. The body immobilization and support device as claimed in claim 1, wherein a cushioning means, which has a similar shape to said shell, lines the inside surface of the shell.

4. The body immobilization and support device as claimed in claim 3, wherein said cushioning means is integral with said shell.

5. The body immobilization and support device as claimed in claim 1, wherein said shoulder engaging means is unitarily attached to said shell at one end, and has a curved portion which curves from where it is attached to said shell, upward and away from said shell, said curved portion conforming to a patient's shoulders.

* * * * *